US006767563B2

United States Patent
Farley

(10) Patent No.: US 6,767,563 B2
(45) Date of Patent: *Jul. 27, 2004

(54) IMMUNE FUNCTIONS

(76) Inventor: Michael D. Farley, 225 Fifth Ave., Suite 6, Indiatlantic, FL (US) 32903

(*) Notice: Subject to any disclaimer, the term of this patent is extended or adjusted under 35 U.S.C. 154(b) by 0 days.

This patent is subject to a terminal disclaimer.

(21) Appl. No.: 10/234,987

(22) Filed: Aug. 26, 2002

(65) Prior Publication Data

US 2003/0082203 A1 May 1, 2003

Related U.S. Application Data

(63) Continuation of application No. 10/012,853, filed on Oct. 30, 2001, now abandoned.

(51) Int. Cl.$^7$ ................................................ A61K 35/78

(52) U.S. Cl. .................. 424/729; 424/451; 424/195.15; 424/756; 514/2

(58) Field of Search ................................. 424/729, 451, 424/195.15, 756; 514/2

(56) References Cited

U.S. PATENT DOCUMENTS 6,544,564 B1 * 4/2003 Farley

* cited by examiner

*Primary Examiner*—Francisco Prats
*Assistant Examiner*—Susan D. Coe
(74) *Attorney, Agent, or Firm*—Bidyut K. Niyogi; Transnational Enerprise Inc.

(57) ABSTRACT

An inventive and proprietary food supplement formula per unit to enhance the body's natural immune function against viral and infectious diseases and cancer. The food supplement per unit in liquid or capsule gel caplets consists of:

200 to 600 mg. of Chrysin;
200 to 600 mg. of Coriolus Versicolor PSK;
50 to 150 mg. of 3,3' Diindolylmethane DIM;
50 to 150 mg. of Resveratrol 25 %;
50 to 150 mg. Turmeric Extract 95 %;
40 to 140 mg. Green Tea Extract 95 %;
20 to 80 mg. of Quercitin Dihydrate 99 %; and
15 to 75 mg. of Phosphatidyl Choline 50 %.

Advantageously, each dose unit preferably includes 25 mg to about 150 mgs. of Myricetin.

4 Claims, No Drawings

IMMUNE FUNCTIONS

This is a Continuation Patent Application of pending patent application Ser. No. 10/012,853, filed Oct. 30, 2001 now abandoned to replace it.

This invention relates to an immunity system of a human body, against viral and infectious disease and cancer.

The immune function is a system that functions to include absorption of excess fluid and its return to the blood stream, absorption of fat and finally to the immune system function.

Immnunity is the body's capability to repel foreign substances and cells. The non specific responses are the first line of defense. Highly specific responses are the second line of defenses and are tailored to an individual threat.

According to the present invention, a food supplement per unit in liquid or capsule gel caplets, characterized in that each dose unit in compound form consists of:
- (a) 200 to 600 mg. of Chrysin
- (b) 200 to 600 mg. of Coriolus Versicolor (PSK)
- (c) 50 to 150 mg. of 3,3' Diindolymethane (DM)
- (d) 50 to 150 mg. of Resveratrol 25%
- (e) 50 to 150 mg. of Turmeric Extract 95%
- (f) 40 to 140 mg. of Green Tea Extract 95%
- (g) 20 to 80 mg. of Quercitin Dihydrate 99%
- (h) 15 to 75 mg. of Phosphatidyl Choline 50%

Preferably the invention may also include 25 mg. to about 150 mg. of Myricetin.

The present invention advantageously includes a method of processing a food supplement in the form of a broth by the steps for each food supplement unit including:
- (a) combining 40 to 140 mg. of Green Tea Extract 95% with about 200 to 600 mg. of Coriolus Versicolor (PSK) and about 200 to 600 mg. of Chrysin;
- (b) treating 50 to 150 mg. of Turmeric Extract 95% in powder form with about 20 to 80 mg. Quercitin Dihydrate 99% as a mixture of Turmeric and Quercitin Dihydrate;
- (c) further combining 15 to 75 mg. of Phosphatidyl Choline 50% with about 50 to 150 mg. of 3,3' Diindolyemethane (DIM) and 50 to 150 mg. Of Resveratrol 25' with the mixture of (b); and
- (d) combining the steps of the products or mixtures resulting from (a); (b); and (c) and mixing the portions whereby it is mixed with an edible liquid so as to form a food supplement broth.

These all natural formulas contain phytochemicals that have been shown to cause cell apoptosis, cytotoxicity and inhibition of replication in all of the following cancer cell lines.

THP-1 human monocytic leukaemia cells
CaCo-2 human colon cancer cells
Human leukaemia HL-60 cells
HLA B40- positive breast cancer cells
Estrogen receptor positive MCF-7 (human breast cancer cell lines)
Estrogen receptor negative MDA-MB-468 (human breast cancer cell lines)
Squamous cell carcinoma (SCC) (oral)
Androgen-sensitive LNCaP (human prostrate)
Androgen-insensitive PC-3 cell lines (human prostrate)

These phytochemicals have also been tested and found to be effective against the HIV and Herpes viruses. It dunctions on two levels. On one level it acts directly and positively on the immune system. It does this be increasing the number and function of the body's own natural killer cells as well as by increasing the number and function of lymphocytes. For this reason, it may be one of the most effective prophylactics against cancer and viral infections available on the market.

The phytochemicals are suspended in liposome's to enhance bioavailability. This same technology is currently being used to enhance the efficacy of some chemotherapeutic agents. It offers as much more direct presentation of the desired phytochemicals to the lymphatic system.

However, the present invention plays a totally new role to stabilize and form within the body's natural immune function system and enhanced defense mechanism against viral infectious disease and cancer.

The present formula can be converted into capsule gel caplets, making it easier to give to a patient, in lieu of the liquid dosage.

An inventive and proprietary formula also known as Dr. Farley's broth assists to enhance the body's natural immune function against viral and infectious diseases and cancer. The composition per unit dose in liquid or capsule gel caplets consists of:
- (a) 200 to 600 mg. of Chrysin
- (b) 200 to 600 mg. of Coriolus Versicolor (PSK)
- (c) 50 to 150 mg. of 3,3' Diindolymethane (DM)
- (d) 50 to 150 mg. of Resveratrol 25%
- (e) 50 to 150 mg. of Turmeric Extract 95%
- (f) 40 to 140 mg. of Green Tea Extract 95%
- (g) 20 to 80 mg. of Quercitin Dihydrate 99%
- (h) 15 to 75 mg. of Phosphatidyl Choline 50%

Advantageously, each dose unit preferably includes 25 mg. to about 150 mg. of Myricetin.

What is claimed is:

1. A method for making a food supplement composition consisting of:
- (A) combining 40 to 140 mg of Green Tea extract 95% with about 200 to 600 mg of Coriolus Versicolor PSK and about 200 to 600 mg of Chrysin;
- (B) combining 50 to 150 mg of powdered Turmeric extract 95% with about 20 to 80 mg of Quercitin Dihydrate 99%;
- (C) combining 15 to 75 mg of Phosphatidyl Choline 50% with about 50 to 150 mg of 3,3' Diindolylmethane (DIM) and 50 to 150 mg of Resveratrol 25%; and
- (D) combining the mixtures resulting from steps (A), (B), and (C) together to form a food supplement unit; and
- (E) combining the food supplement unit with an edible liquid so as to form a food supplement broth.

2. The method for making a food supplement composition as claimed in claim 1, wherein the food supplement unit further consists of about 25 mg to 150 mg of Myricetin.

3. The method for making a food supplement composition as claimed in claim 1, wherein the food supplement unit consists of:
- a. 90 mg Green Tea extract 95%;
- b. 400 mg Coriolus Versicolor PSK;
- c. 400 mg Chrysin;
- d. 100 mg Turmeric extract 95%;
- e. 50 mg Quercitin dihydrate 99%;
- f. 40 mg Phosphatidyl choline 50%;
- g. 100 mg 3,3' Diindolylmethane (DIM); and
- h. 100 mg Resveratrol 25%.

4. The method for making a food supplement composition as claimed in claim 3, wherein the food supplement unit further consists of 100 mg Myricetin.

* * * * *